(12) United States Patent
Luesch et al.

(10) Patent No.: US 10,010,569 B2
(45) Date of Patent: Jul. 3, 2018

(54) SEAWEED EXTRACTS, UNSATURATED FATTY ACIDS, AND METHODS OF TREATMENT

(71) Applicant: University of Florida Research Foundation, Inc., Gainesville, FL (US)

(72) Inventors: Hendrik Luesch, Gainesville, FL (US); Valerie J. Paul, Fort Pierce, FL (US); Rui Wang, Gainesville, FL (US)

(73) Assignees: University of Florida Research Foundation, Incorporated, Gainesville, FL (US); Smithsonian Institution, Washington, DC (US)

( * ) Notice: Subject to any disclaimer, the term of this patent is extended or adjusted under 35 U.S.C. 154(b) by 165 days.

(21) Appl. No.: 14/441,744

(22) PCT Filed: Nov. 6, 2013

(86) PCT No.: PCT/US2013/068726
§ 371 (c)(1),
(2) Date: May 8, 2015

(87) PCT Pub. No.: WO2014/074592
PCT Pub. Date: May 15, 2014

(65) Prior Publication Data
US 2015/0290264 A1    Oct. 15, 2015

Related U.S. Application Data

(60) Provisional application No. 61/724,187, filed on Nov. 8, 2012.

(51) Int. Cl.
| | |
|---|---|
| *A61K 36/00* | (2006.01) |
| *A61K 36/05* | (2006.01) |
| *A61K 45/06* | (2006.01) |
| *A61K 31/16* | (2006.01) |
| *A61K 31/201* | (2006.01) |
| *A61K 9/00* | (2006.01) |
| *A61K 9/06* | (2006.01) |
| *C07C 59/76* | (2006.01) |
| *C07C 235/76* | (2006.01) |

(52) U.S. Cl.
CPC ............ *A61K 36/05* (2013.01); *A61K 9/0014* (2013.01); *A61K 9/06* (2013.01); *A61K 31/16* (2013.01); *A61K 31/201* (2013.01); *A61K 45/06* (2013.01); *C07C 59/76* (2013.01); *C07C 235/76* (2013.01); *A61K 2236/00* (2013.01)

(58) Field of Classification Search
CPC .................................................. A61K 36/00
USPC ........................................................ 424/725
See application file for complete search history.

(56) References Cited

U.S. PATENT DOCUMENTS

| | | |
|---|---|---|
| 2004/0023924 A1 | 2/2004 | Lienart |
| 2004/0170645 A1 | 9/2004 | Daniels |
| 2007/0003536 A1 | 1/2007 | Zimmerman et al. |
| 2010/0255025 A1 | 10/2010 | Majmudar |
| 2013/0164324 A1* | 6/2013 | Majmudar ............... A61K 8/97 |
| | | 424/195.17 |
| 2016/0051604 A1 | 2/2016 | Luesch et al. |
| 2017/0056317 A1* | 3/2017 | Athwal .................... A61K 8/73 |

OTHER PUBLICATIONS

International Search Report and Written Opinion dated Aug. 7, 2014 in connection with PCT/US2014/029314.
Jeong et al., Nrf2: a potential molecular target for cancer chemoprevention by natural compounds, Antioxid Redox Signal. Jan.-Feb. 2006;8(1-2):99-106. Review.
Kajiwara et al., Antimicrobial browning-inhibitory effect of flavor compounds in seaweeds, Journal of Applied Phycology, Jun. 30, 2006; 18(3):413-22. doi:10.1007/s10811-006-9046-6.
Ratnayake et al., Cultivated sea lettuce is a multiorgan protector from oxidative and inflammatory stress by enhancing the endogenous antioxidant defense system. Cancer Prev Res (Phila). Sep. 2013;6(9):989-99. doi:10.1158/1940-6207.
Ryu et al, The green algae Ulva fasciata Delile extract induces apoptotic cell death in human colon cancer cells. In Vitro Cell Dev Biol Anim. Jan. 2013;49(1):74-81. doi: 10.1007/s11626-012-9547-3. Epub Jan. 9, 2013.
Vijayavel et al., In vitro antioxidant and antimicrobial activities of two Hawaiian marine Limu: Ulva fasciata (Chlorophyta) and Gracilaria salicornia (Rhodophyta). J Med Food. Dec. 2010;13(6):1494-9. doi: 10.1089/jmf.2009.0287.
Wang et al., Seaweed extracts and unsaturated fatty acid constituents from the green alga Ulva lactuca as activators of the cytoprotective Nrf2-ARE pathway. Free Radic Biol Med. Apr. 2013;57:141-53. doi:10.1016/j.freeradbiomed.2012.12.019. Epub Jan. 4, 2013.

(Continued)

*Primary Examiner* — Michael V Meller
(74) *Attorney, Agent, or Firm* — Wolf, Greenfield & Sacks, P.C.

(57) ABSTRACT

The instant invention relates to seaweed extract compositions, processes for isolation, isolated active agents, and methods of treating disease, disorders and conditions in a subject, including, reactive oxygen species (ROS)-mediated diseases and diseases mediated through the activation of the Nrf2-ARE (antioxidant response element) pathway, including proliferative diseases and disorders, Alzheimer's disease, stroke, and certain diseases and disorders of aging and associated with aging and exposure, by use of the extracts, compounds, and compositions thereof.

1 Claim, 6 Drawing Sheets

(56) References Cited

OTHER PUBLICATIONS

International Search Report of PCT/US2013/068726 dated Feb. 10, 2014.
Awad, N.E., Biologically Active Steroid From the Green Alga Ulva lactuca, Phytotherapy Research 2000, vol. 14, pp. 641-643.
International Preliminary Report on Patentability and Written Opinion for PCT/US2013/068726 dated May 12, 2015.
U.S. Appl. No. 14/846,544, filed Sep. 4, 2015, Luesch et al.
PCT/US2014/029314, dated Aug. 7, 2014, International Search Report and Written Opinion.

* cited by examiner

7(*E*)-9-keto-octadec-7-enoic acid (1):  $R_1$ = OH,  $R_2$ = $C_2H_5$
7(*E*)-9-keto-hexadec-7-enoic acid (2):  $R_1$ = OH,  $R_2$ = H
7(*E*)-9-keto-octadec-7-enamide (3):    $R_1$ = $NH_2$,  $R_2$ = $C_2H_5$

SEAWEED EXTRACTS, UNSATURATED FATTY ACIDS, AND METHODS OF TREATMENT

CROSS REFERENCE TO RELATED APPLICATIONS

This application is the U.S. National Stage. pursuant to 35 U.S.C. § 371, of U.S. International Application N. PCT/US2013/068726, filed Nov. 6, 2013, which claims the benefit of U.S. Provisional Application No. 61/724,187 filed on Nov. 8, 2012, the entire disclosures of which are is hereby incorporated in their entirety.

STATEMENT OF RIGHTS TO INVENTIONS MADE UNDER FEDERALLY SPONSORED RESEARCH

The invention was made with government support under Grant Nos. CA133681 and EY020825 awarded by the National Institutes of Health. The government has certain rights in the invention.

BACKGROUND

This invention relates to seaweed extract compositions, enriched active fractions, isolated active agents, and methods of use for the treatment of reactive oxygen species (ROS)-mediated diseases and diseases alleviated or prevented through the activation of the Nrf2-ARE (antioxidant response element) pathway, such as inflammation, cancer, Alzheimer's disease and other neurodegenerative disorders, stroke, chronic kidney disease, type II diabetes, and aging itself.

In aerobes, reactive oxygen species (ROS) is produced during cellular respiration and energy metabolism [Halliwell, B. Biochemistry of oxidative stress. *Biochem Soc Trans.* 35:1147-50; 2007]. In a healthy cell, the level of ROS is tightly regulated by the antioxidant defense system. However, upon environmental stress or cellular damage, the cell cannot readily detoxify the ROS generated and may thereby suffer from oxidative stress, which is implicated in the pathogenesis of many age-related diseases, such as inflammation, cancer, Alzheimer's disease and other neurodegenerative disorders, stroke, chronic kidney disease, type II diabetes, and aging itself [Liu, Y.; Kern, J. T.; Walker, J. R.; Johnson, J. A.; Schultz, P. G.; Luesch, H. A genomic screen for activators of the antioxidant response element. *Proc Natl Acad Sci USA.* 104:5205-10; 2007; Dinkova-Kostova A T, Massiah M A, Bozak R E, Hicks R J, Talalay P. Potency of Michael reaction acceptors as inducers of enzymes that protect against carcinogenesis depends on their reactivity with sulfhydryl groups. Proc Natl Acad Sci USA 2001; 98:3404-3409; Ramos-Gomez M, Kwak M-K, Dolan P M, Itoh K, Yamamoto M, Talalay P et. al. Sensitivity to carcinogenesis is increased and chemoprotective efficacy of enzyme inducers is lost in nrf2 transcription factor-deficient mice. Proc Natl Acad Sci USA 2001; 98:3410-3415; van Muiswinkel F L, Kuiperij H B. The Nrf2-ARE signaling pathway: promising drug target to combat oxidative stress in neurodegenerative disorders. Curr Drug Targets CNS Neurol Disord 2005; 4:267-281; Dinkova-Kostova, A T, Liby K T, Stephenson K K, Holtzclaw W D, Gao X, Suh N et. al. Extremely potent triterpenoid inducers of the phase 2 response: Correlations of protection against oxidant and inflammatory stress. Proc Natl Acad Sci USA 2005; 102: 4584-4589; Chen X-L, Kunsch C. Induction of cytoprotective genes through Nrf2/antioxidant response element pathway: a new therapeutic approach for the treatment of inflammatory diseases. Curr Pharm Des 2004; 10:879-891; Pergola P E, Raskin P, Toto R D, Meyer C J, Huff J W, Grossman E B et. al. BEAM Study Investigators. Bardoxolone methyl and kidney function in CKD with type 2 diabetes. N Engl J Med 2011; 365:327-3361.

One of the major defense systems employed by the cell to counteract oxidative insult is the Nrf2-ARE signaling pathway. Under normal conditions, the Kelch-like ECH-associated protein 1 (Keap1) sequesters the nuclear factor E2-related factor 2 (Nrf2) in the cytoplasm and targets it for proteasomal degradation. When the oxidative stress sensor Keap1 encounters reactive oxygen species or electrophilic chemicals, Nrf2 is stabilized and released. The transcriptional activator (Nrf2) translocates to the nucleus where it binds to the antioxidant response element (ARE), initiating the expression of cytoprotective enzymes such as NAD(P) H:quinone oxidoreductase 1 (NQO1), and glutathione S-transferase (GST) [Mang, D. D. Mechanistic studies of the Nrf2-Keap1 signaling pathway. *Drug Metab Rev.* 38:769-89; 2006; Kobayashi, M.; Yamamoto, M. Nrf2-Keap1 regulation of cellular defense mechanisms against electrophiles and reactive oxygen species. *Adv Enzyme Regul.* 46:113-40; 2006; Dinkova-Kostova, A. T.; Holtzclaw, W. D.; Kensler, T. W. The role of Keap1 in cellular protective responses. *Chem Res Toxicol.* 18:1779-91; 20051.

Many naturally occurring small molecule inducers of the Nrf2-ARE pathway have been identified and explored as chemopreventive or therapeutic agents. For example, curcumin [Balogun, E.; Hoque, M.; Gong, P.; Killeen, E.; Green, C. J.; Foresti, R.; Alam, J.; Motterlini, R. Curcumin activates the haem oxygenase-1 gene via regulation of Nrf2 and the antioxidant-responsive element. *Biochem J.* 371: 887-95; 2003], the active ingredient in traditional herbal remedy and dietary spice turmeric (*Curcuma longa*) is currently in clinical trials for multiple conditions, including several cancers and Alzheimer's disease [Hatcher, H.; Planalp, R.; Cho, J.; Torti, F. M.; Torti, S. V. Curcumin: from ancient medicine to current clinical trials. *Cell Mol Life Sci.* 65:1631-52; 2008]. The skin of red grapes (*Vitis vinifera*) is rich in resveratrol [Langcake, P.; Pryce, R. J. Production of Resveratrol by *Vitis-Vinifera* and Other Members of Vitaceae as a Response to Infection or Injury. *Physiological Plant Pathology.* 9:77-86; 1976; Rubiolo, J. A.; Mithieux, G.; Vega, F. V. Resveratrol protects primary rat hepatocytes against oxidative stress damage: activation of the Nrf2 transcription factor and augmented activities of antioxidant enzymes. *Eur J Pharmacol.* 591:66-72; 2008], which was found to be responsible for an inverse relationship between grape consumption and breast cancer occurrence in an epidemiologic study [Levi, F.; Pasche, C.; Lucchini, F.; Ghidoni, R.; Ferraroni, M.; La Vecchia, C. Resveratrol and breast cancer risk *Eur J Cancer Prev.* 14:139-42; 2005]. In a clinical setting, resveratrol was observed to induce the re-expression of tumor suppressor genes in a group of women who are at increased risk of breast cancer [Zhu, W.; Qin, W.; Zhang, K.; Rottinghaus, G. E.; Chen, Y. C.; Kliethermes, B.; Sauter, E. R. Trans-resveratrol alters mammary promoter hypermethylation in women at increased risk for breast cancer. *Nutr Cancer.* 64:393-400; 2012]. The detoxification enzyme inducer, sulforaphane [Kensler, T. W.; Egner, P. A.; Agyeman, A. S.; Visvanathan, K.; Groopman, J. D.; Chen, J. G.; Chen, T. Y.; Fahey, J. W.; Talalay, P. Keap1-Nrf2 Signaling: A Target for Cancer Prevention by Sulforaphane. *Top Curr Chem.* 2012], was found in many cruciferous vegetables. It has been shown that a daily regimen of hot water infused with 3-day-old broccoli sprouts has promising results in cancer chemoprevention in healthy individuals [Kensler, T. W.; Chen, J. G.; Egner, P. A.; Fahey, J. W.; Jacobson, L. P.; Stephenson, K. K.; Ye, L.; Coady, J. L.; Wang, J. B.; Wu, Y.; Sun, Y.; Zhang, Q. N.; Zhang, B. C.; Zhu, Y. R.; Qian, G. S.; Carmella, S. G.; Hecht, S. S.; Benning, L.; Gange, S. J.; Groopman, J. D.; Talalay, P. Effects of glucosinolate-rich broccoli sprouts on urinary levels of aflatoxin-DNA adducts and phenanthrene tetraols in a randomized clinical trial in He Zuo township, Qidong, People's Republic of China. *Cancer Epidemiol Biomarkers Prev.* 14:2605-13; 2005]. Broccoli sprouts (*Brassica oleracea italica*) contain high levels of its precursor, glucoraphanin [Farnham, M. W.; Stephenson, K. K.; Fahey, J. W. Glucoraphanin level in broccoli seed is largely determined by genotype. *Hortscience.* 40:50-53; 2005], which can be enzymatically converted to sulforaphane in the gastrointestinal tract after ingestion [Zhang, Y.; Talalay, P.; Cho, C. G.; Posner, G. H. A major inducer of anticarcinogenic protective enzymes from broccoli: isolation and elucidation of structure. *Proc Natl Acad Sci USA.* 89:2399-403; 1992].

The marine environment has also proven to be a rich source of potent compounds with diverse therapeutic properties [Newman, D. J.; Cragg, G. M. Marine natural products and related compounds in clinical and advanced preclinical trials. *J Nat Prod.* 67:1216-38; 2004; Montaser, R.; Luesch, H. Marine natural products: a new wave of drugs? *Future Med Chem.* 3:1475-89; 2011]. For example, several molecules with anti-cancer activities based on leads from marine cyanobacteria have been described [Taori, K.; Paul, V. J.; Luesch, H. Structure and activity of largazole, a potent antiproliferative agent from the Floridian marine *cyanobacterium Symploca* sp. *J Am Chem Soc.* 130:1806-7; 2008-20; Hong, J.; Luesch, H. Largazole: from discovery to broad-spectrum therapy. *Nat Prod Rep.* 29:449-56; 2012; Chen, Q. Y.; Liu, Y.; Luesch, H. Systematic Chemical Mutagenesis Identifies a Potent Novel Apratoxin A/E Hybrid with Improved in Vivo Antitumor Activity. *ACS Med Chem Lett.* 2:861-865; 2011]. Additionally, the free radical scavenger fucoxanthin, a carotenoid from a common edible seaweed, *Hijikia fusiformis* [Yan, X.; Chuda, Y.; Suzuki, M.; Nagata, T. Fucoxanthin as the major antioxidant in *Hijikia fusiformis*, a common edible seaweed. *Biosci Biotechnol Biochem.* 63:605-7; 1999], was found to activate the antioxidant defense system (Nrf2/ARE) in mouse liver cells.

However, despite these developments, there exists an unmet need for additional antioxidants and for additional treatments for ROS-mediated diseases. As a result of ongoing investigations to identify new drug leads from marine sources, we report seaweed extract compositions isolated from the green alga *Ulva lactuca*, processes for isolation, enriched active fractions, and isolated active agents. The extracts, enriched active extracts, and compounds herein are found to be activators of the cytoprotective Nrf2-ARE pathway. These findings provide new alternatives for the treatment of reactive oxygen species (ROS)-mediated diseases and diseases alleviated or prevented through the activation of the Nrf2-ARE (antioxidant response element) pathway, such as inflammation, cancer, Alzheimer's disease and other neurodegenerative disorders, stroke, chronic kidney disease, type II diabetes, and aging itself.

BRIEF SUMMARY OF THE INVENTION

This invention is directed towards seaweed extract compositions, enriched active extracts, processes for isolation, isolated active agents, and methods of treating disease, disorders and conditions in a subject, including, reactive oxygen species (ROS)-mediated diseases and diseases alleviated or prevented through the activation of the Nrf2-ARE (antioxidant response element) pathway, including proliferative diseases and disorders, inflammation, Alzheimer's disease and other neurodegenerative disorders, stroke, chronic kidney disease, type II diabetes, and certain diseases and disorders of aging and associated with aging and exposure, by use of the extracts, enriched active extracts, compounds, and compositions thereof.

This invention is directed towards seaweed extract compositions, enriched active extracts, processes for isolation, isolated active agents, methods for activating the Nrf2-ARE pathway, and methods of treating reactive oxygen species (ROS)-mediated diseases and diseases alleviated or prevented through the activation of the Nrf2-ARE (antioxidant response element) pathway, including proliferative diseases and disorders, inflammation, cancer, Alzheimer's disease and other neurodegenerative disorders, stroke, chronic kidney disease, type II diabetes, and aging itself.

Another aspect of this invention is a composition comprising a seaweed extract herein (e.g., extract of *Ulva lactuca*). Another aspect is a composition comprising an enriched active extract from a seaweed extract herein. Another aspect is a composition comprising an isolated compound from a seaweed extract herein.

In one embodiment, the compound (or combinations of compounds) delineated herein is obtained from a procedure comprising extraction from seaweed. In certain embodiments, the procedure for use in obtaining the compound (or combinations of compounds) further includes any of isolation, enrichment, evaporation, and partitioning steps of the seaweed extracts.

Another aspect of this invention is a pharmaceutical composition comprising a seaweed extract herein or a compound that occurs in a seaweed extract herein.

In one embodiment, the invention provides an extract from seaweed isolated by:
  a). exposing said seaweed to a solvent or solvent combination;
  b). filtering the material/mixture from step a);
  c). removing the solvent or solvent combination from b) to afford a residue;
  d). partitioning said residue between an organic solvent or organic solvent combination and water;
  e). separating the organic phase and the water phase from d);
  f). removing the organic solvent or organic solvent combination from the said organic phase from e);
  g). purifying the material/mixture from f) using chromatography and collecting fractions.

Another aspect is where the material/mixture from step g) is analyzed by high-performance liquid chromatography (HPLC). Another aspect is where the solvent or solvent combination in extraction step a) is selected from the group consisting of ethyl acetate, methanol, hexanes, ethanol, isopropanol, acetonitrile, water, and dichloromethane. Another aspect is where the solvent or solvent combination in extraction step a) is selected from the group consisting of ethyl acetate and methanol. Another aspect is where steps a)-c) are repeated with the same or different solvent or solvent combination as used in the previous iteration(s). Another aspect is where the organic solvent or organic solvent combination in extraction step d) is ethyl acetate. Another aspect is where the seaweed is the green alga *Ulva lactuca*.

In another embodiment, the invention provides an extract from seaweed isolated by:
i. exposing said seaweed to a solvent or solvent combination;
ii. filtering the material/mixture from step i;
iii. removing the solvent or solvent combination from ii to afford a residue;
iv. purifying the material/mixture from iii using chromatography and collecting fractions.

Another aspect is where the material/mixture in step iv is analyzed by high-performance liquid chromatography (HPLC). Another aspect is where the solvent or solvent combination in extraction step i is selected from the group consisting of ethyl acetate, methanol, hexanes, ethanol, isopropanol, acetonitrile, water, and dichloromethane. Another aspect is where the solvent or solvent combination in extraction step i is selected from the group consisting of ethyl acetate and methanol. Another aspect is where steps i-iii are repeated with the same or different solvent or solvent combination as used in the previous iteration(s). Another aspect is where the seaweed is the green alga *Ulva lactuca*.

In another embodiment, the invention provides an extract from seaweed isolated by:
(i) exposing said seaweed to a solvent or solvent combination;
(ii) filtering the material/mixture from step (i);
(iii) removing the solvent or solvent combination from (ii) to afford a residue;
(iv) purifying the material/mixture from (iii) using chromatography and collecting fractions.

Another aspect is where the solvent or solvent combination in extraction step (i) is selected from the group consisting of ethyl acetate, methanol, hexanes, ethanol, isopropanol, acetonitrile, water, and dichloromethane. Another aspect is where the solvent or solvent combination in extraction step (i) is selected from the group consisting of ethyl acetate and methanol. Another aspect is where steps (i)-(iii) are repeated with the same or different solvent or solvent combination as used in the previous iteration(s). Another aspect is where the seaweed is the green alga *Ulva lactuca*.

In another embodiment, the invention provides an extract from seaweed isolated by:
[a]. exposing said seaweed to a solvent or solvent combination;
[b]. filtering the material/mixture from step [a].

Another aspect is where the solvent or solvent combination in extraction step [a] is selected from the group consisting of ethyl acetate, methanol, hexanes, ethanol, isopropanol, acetonitrile, water, and dichloromethane. Another aspect is where the solvent or solvent combination in extraction step [a] is selected from the group consisting of ethyl acetate and methanol. Another aspect is where steps [a]-[b] are repeated with the same or different solvent or solvent combination as used in the previous iteration(s). Another aspect is where the seaweed is the green alga *Ulva lactuca*.

In another embodiment, the invention provides an extract from seaweed isolated by:
((a)). exposing said seaweed to a solvent or solvent combination;
((b)). filtering the material/mixture from step ((a)).

Another aspect is where the material/mixture in step ((b)) is analyzed by high-performance liquid chromatography (HPLC). Another aspect is where the solvent or solvent combination in extraction step ((a)) is selected from the group consisting of ethyl acetate, methanol, hexanes, ethanol, isopropanol, acetonitrile, water, and dichloromethane. Another aspect is where the solvent or solvent combination in extraction step ((a)) is selected from the group consisting of ethyl acetate and methanol. Another aspect is where steps ((a))-((b)) are repeated with the same or different solvent or solvent combination as used in the previous iteration(s). Another aspect is where the seaweed is the green alga *Ulva lactuca*.

In another embodiment, the invention provides an extract from seaweed isolated by:
((i)) exposing said seaweed to a solvent or solvent combination;
((ii)) filtering the material/mixture from step ((i));
((iii)) removing the solvent or solvent combination from the product of ((ii)) to afford a residue;
((iv)) purifying the material/mixture from ((iii)) using chromatography and collecting fractions;
((v)) analyzing the fractions from step ((iv)) by high-performance liquid chromatography (HPLC);
((vi)) removing the chromatography mobile phase from fractions from step ((v));
((vii)) purifying the material/mixture from ((vi)) using chromatography and collecting fractions.

Another aspect is where the material/mixture in step ((vii)) is analyzed by high-performance liquid chromatography (HPLC). Another aspect is where the solvent or solvent combination in extraction step ((i)) is selected from the group consisting of ethyl acetate, methanol, hexanes, ethanol, isopropanol, acetonitrile, water, and dichloromethane. Another aspect is where the solvent or solvent combination in extraction step ((i)) is selected from the group consisting of ethyl acetate and methanol. Another aspect is where steps ((i))-((iii)) are repeated with the same or different solvent or solvent combination as used in the previous iteration(s). Another aspect is where the seaweed is the green alga *Ulva lactuca*.

Another aspect is a compound or extract obtained by one or more steps of the processes or procedures delineated herein, including specifically as delineated in the Examples herein.

Another aspect is where the seaweed extract comprises one or more compounds selected from 7(E)-9-keto-octadec-7-enoic acid (1), 7(E)-9-keto-hexadec-7-enoic acid (2), or 7(E)-9-keto-octadec-7-enamide (3).

Another aspect is where the seaweed extract is enriched in one or more compounds selected from 7(E)-9-keto-octadec-7-enoic acid (1), 7(E)-9-keto-hexadec-7-enoic acid (2), or 7(E)-9-keto-octadec-7-enamide (3).

Another aspect is where the seaweed extract comprises 7(E)-9-keto-octadec-7-enoic acid (1).

In another embodiment the invention provides a compound that is:
7(E)-9-keto-octadec-7-enoic acid (1);
7(E)-9-keto-hexadec-7-enoic acid (2); or
7(E)-9-keto-octadec-7-enamide (3).

Another aspect is where the compound is 7(E)-9-keto-octadec-7-enoic acid (1).

In another aspect the invention provides an isolated compound that is selected from the group of 7(E)-9-keto-octadec-7-enoic acid (1) and compound 7(E)-9-keto-hexadec-7-enoic acid (2).

In another aspect, the invention provides a pharmaceutical composition comprising a seaweed extract and a pharmaceutically acceptable carrier.

In another aspect, the invention provides a pharmaceutical composition comprising an enriched seaweed extract and a pharmaceutically acceptable carrier.

In other aspects, the invention provides a method of treating a disease, disorder, or symptom thereof in a subject, comprising administering to the subject any compound or seaweed extract herein. In another aspect, the compound or seaweed extract is administered in an amount and under conditions sufficient to ameliorate the disease, disorder, or symptom thereof in a subject. In another aspect, the disease, disorder, or symptom includes proliferative diseases and disorders, inflammation, cancer, Alzheimer's disease and other neurodegenerative disorders, stroke, chronic kidney disease, type II diabetes, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro) proliferative disorders, and aging itself.

In other aspects, the invention provides a method of modulating Nrf2-ARE activity in a subject, comprising contacting the subject with any compound or seaweed extract herein, in an amount and under conditions sufficient to modulate Nrf2-ARE activity. In another aspect, the modulation is activation.

In other aspects, the invention provides a method of modulating the proliferation activity in a subject, comprising contacting the subject with any compound or seaweed extract herein, in an amount and under conditions sufficient to modulate proliferation activity.

In one aspect, the invention provides a method of treating a subject suffering from or susceptible to a proliferation related disorder or disease, comprising administering to the subject an effective amount of a compound or seaweed extract or pharmaceutical composition of any compound or seaweed extract herein.

In another aspect, the invention provides a method of treating a subject suffering from or susceptible to a ROS-mediated disorder or disease, comprising administering to the subject an effective amount of a compound or seaweed extract or pharmaceutical composition of any compound or seaweed extract herein.

In another aspect, the invention provides a method of treating a subject suffering from or susceptible to a disorder or disease alleviated or prevented through the Nrf2-ARE pathway, comprising administering to the subject an effective amount of a compound or seaweed extract or pharmaceutical composition of any compound or seaweed extract herein. Another aspect is where the disorder or disease alleviated or prevented through the Nrf2-ARE pathway includes proliferative diseases and disorders, inflammation, cancer, Alzheimer's disease and other neurodegenerative disorders, stroke, chronic kidney disease, type II diabetes, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders and aging itself.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or seaweed extract or pharmaceutical composition of any compound or seaweed extract herein, such that said subject is treated for said disorder.

In another aspect, the invention provides a method of treating a subject suffering from or susceptible to a ROS activity related disorder or disease, wherein the subject has been identified as in need of treatment for a ROS related disorder or disease, comprising administering to said subject in need thereof, an effective amount of a compound or seaweed extract or pharmaceutical composition of any compound or seaweed extract herein, such that said subject is treated for said disorder.

In another aspect, the invention provides a method of treating a subject suffering from or susceptible to a Nrf2-ARE activity related disorder or disease, wherein the subject has been identified as in need of treatment for a Nrf2-ARE related disorder or disease, comprising administering to said subject in need thereof, an effective amount of a compound or seaweed extract or pharmaceutical composition of any compound or seaweed extract herein, such that said subject is treated for said disorder. Another aspect is where the said disorder includes proliferative diseases and disorders, inflammation, cancer, Alzheimer's disease and other neurodegenerative disorders, stroke, chronic kidney disease, type II diabetes, and aging itself.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or seaweed extract or pharmaceutical composition of any compound or seaweed extract herein, such that cell proliferation in said subject is modulated (e.g., down regulated). In another aspect, the compounds or seaweed extracts delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of any compound or seaweed extract delineated herein, and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

In a specific aspect, the invention provides a method of treating inflammation, Alzheimer's disease and other neurodegenerative disorders, stroke, chronic kidney disease, type II diabetes, aging itself, and other diseases mediated through ROS, comprising administering to said subject in need thereof, an effective amount of any compound or seaweed extract delineated herein, and pharmaceutically acceptable salts thereof.

In another aspect, the invention provides a method of treating diseases, disorders, or symptoms thereof mediated by activation of the Nrf2-ARE pathway in a subject in need thereof comprising administering to said subject, an effective amount of any compound or seaweed extract delineated herein, and pharmaceutically acceptable salts thereof.

In another aspect, the invention provides a method of treating diseases, disorders, or symptoms in a subject in need thereof comprising administering to said subject, an effective amount of any compound or seaweed extract delineated herein, and pharmaceutically acceptable salts thereof. Such methods are useful for treating memory loss, inducing neurogenesis, enhancing memory retention, enhancing memory formation, increasing synaptic potential or transmission, or increasing long term potentiation (LTP). Such methods are also useful for treating diseases and disorders associated with stem cell fate and that are affected by differentiation, dedifferentiation or transdifferentiation, and thus include but not limited to myogenesis, neurogenesis, osteogenesis and osteoblast maturation.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which.

DETAILED DESCRIPTION

Definitions

Figure 1A:
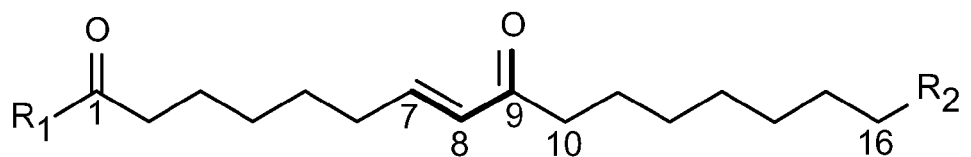
FIG. 1A. depicts chemical structures of compounds 1-3. Structural information of the three compounds isolated from *Ulva lactuca*. (A) Proposed chemical structures.

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

As used herein, "activating" encompasses permitting, increasing and enhancing progression.

As used herein, "enriched" encompasses greater or increased amounts of a material or desired or active compound or agent relative to its natural or other reference state.

As used herein, as "extract" is a preparation of constituents of a material (e.g., seaweed), including for example, solvent extracts, concentrated forms of said constituents, concentrated solvent extracts, isolated chemical compounds or mixtures thereof.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 1000 mg/kg, preferably about 0.1 mg/kg to about 1000 mg/kg, more preferably about 10 mg/kg to about 500 mg/kg of body weight. In other embodiments, the therapeutically effective amount may range from about 0.10 nM to about 500 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

The present invention also contemplates solvates (e.g., hydrates) of a compound of herein, compositions thereof, and their use in the treatment of reactive oxygen species (ROS)-mediated diseases and diseases alleviated or prevented through the activation of the Nrf2-ARE (antioxidant response element) pathway. As used herein, "solvate" refers to the physical association of a compound of the invention with one or more solvent or water molecules, whether organic or inorganic. In certain instances, the solvate is capable of isolation, for example, when one or more solvate molecules are incorporated in the crystal lattice of the crystalline solid.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

This invention is directed towards seaweed extract compositions, enriched active fractions, processes for isolation, isolated active agents, and methods of treating diseases and disorders by use of the extracts, compounds, and compositions delineated herein.

In other aspects, the invention provides a method of treating a disease, disorder, or symptom thereof in a subject, comprising administering to the subject any compound or seaweed extract herein. In another aspect, the compound is administered in an amount and under conditions sufficient to ameliorate the disease, disorder, or symptom thereof in a subject.

The methods can further comprise that wherein the composition is an extract of *Ulva lactuca* or an isolated compound that occurs in a seaweed extract herein.

Another aspect is where the seaweed extract comprises one or more compounds selected from the consisting of 7(E)-9-keto-octadec-7-enoic acid (1), 7(E)-9-keto-hexadec-7-enoic acid (2), and 7(E)-9-keto-octadec-7-enamide (3). Another aspect is where the seaweed extract comprises 7(E)-9-keto-octadec-7-enoic acid (1).

In another aspect the invention provides an isolated compound that is selected from the group of 7(E)-9-keto-octadec-7-enoic acid (1) and compound 7(E)-9-keto-hexadec-7-enoic acid (2).

In other aspects, the invention provides a method of modulating Nrf2-ARE activity in a subject, comprising contacting the subject with any compound or seaweed extract herein, in an amount and under conditions sufficient to modulate Nrf2-ARE activity. In another aspect, the modulation is activation.

In other aspects, the invention provides a method of modulating the proliferation activity in a subject, comprising contacting the subject with any compound or seaweed extract herein, in an amount and under conditions sufficient to modulate proliferation activity.

In one aspect, the invention provides a method of treating a subject suffering from or susceptible to a proliferation related disorder or disease, comprising administering to the subject an effective amount of a compound or seaweed extract or pharmaceutical composition of any compound or seaweed extract herein.

In another aspect, the invention provides a method of treating a subject suffering from or susceptible to a ROS-mediated disorder or disease, comprising administering to the subject an effective amount of a compound or seaweed extract or pharmaceutical composition of any compound or seaweed extract herein.

In another aspect, the invention provides a method of treating a subject suffering from or susceptible to a disorder or disease alleviated or prevented through the Nrf2-ARE pathway, comprising administering to the subject an effective amount of a compound or seaweed extract or pharmaceutical composition of any compound or seaweed extract herein.

Another aspect is where the seaweed is the green alga *Ulva lactuca*.

In certain embodiments, the invention provides a method as described above, wherein the seaweed extract comprises one or more compounds selected from the consisting of 7(E)-9-keto-octadec-7-enoic acid (1), 7(E)-9-keto-hexadec-7-enoic acid (2), and 7(E)-9-keto-octadec-7-enamide (3).

In certain embodiments, the invention provides a method of treating a disorder, wherein the disorder is proliferative diseases and disorders, inflammation, cancer, Alzheimer's disease and other neurodegenerative disorders, stroke, chronic kidney disease, type II diabetes, and aging itself, and other diseases mediated through ROS or alleviated or prevented through the Nrf2-ARE pathway.

In certain embodiments, the methods are useful in providing and/or enhancing anti-aging properties of skin by preventing (e.g., UVA-induced, UVB-induced, photo-damage, aging) wrinkle formation. In certain embodiments, the methods herein are useful in providing and/or enhancing skin tone and skin appearance properties of skin by administration of a topical formulation of compounds and compositions herein to the skin.

In certain embodiments, the compounds and compositions herein are useful in providing and/or enhancing anti-aging properties of skin by preventing (e.g., UVA-induced, UVB-induced, photo-damage, aging) wrinkle formation. In certain embodiments, the compounds and compositions herein are useful in providing and/or enhancing skin tone and skin appearance properties of skin by administration of a topical formulation to the skin.

In certain embodiments, the subject is a mammal, preferably a primate or human.

In another embodiment, the invention provides a method as described above, wherein the effective amount of the compound or seaweed extract ranges from about 0.005 µg/kg to about 500 mg/kg, preferably about 0.1 mg/kg to about 500 mg/kg, more preferably about 10 mg/kg to about 500 mg/kg of body weight.

In other embodiments, the invention provides a method as described above wherein the effective amount of the compound or seaweed extract ranges from about 1.0 nM to about 500 µM. In another embodiment, the effective amount ranges from about 100 nM to about 100 µM.

In other embodiments, the invention provides a method as described above wherein the effective amount of the compound or seaweed extract ranges from about 0.1 mg/ml to about 1000 mg/ml. In certain embodiments, the effective amount ranges from about 1.0 mg/ml to about 500 mg/ml. In another embodiment, the effective amount ranges from about 1.0 mg/ml to about 100 mg/ml.

In another embodiment, the invention provides a method as described above, wherein the compound or seaweed extract is administered intravenously, intramuscularly, subcutaneously, intracerebroventricularly, orally or topically.

In another embodiment, the invention provides a method as described herein wherein the compound or seaweed extract demonstrates selectivity (e.g., at least 2-fold, at least 5-fold, at least 10-fold, at least X-fold where X is any number between 1 and 20 inclusive) in cell growth activity (e.g., in transformed/nontransformed, MDA-MB-231/NMuMG, U2OS/NIH3T3 cells). In another aspect, the compound or seaweed extract demonstrates selectivity in modulating cell growth activity (e.g., at least 2-fold, at least 5-fold, at least 10-fold, at least X-fold where X is any number between 1 and 20 inclusive) relative to another standard anticancer therapy (e.g., paclitaxel, actinomycin D, doxorubicin).

In other embodiments, the invention provides a method as described above, wherein the compound or seaweed extract is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound or seaweed extract as described herein (e.g., of any formulae herein) in the manufacture of a medicament for use in the treatment of a cell proliferation disorder or disease, or to affect cell differentiation, dedifferentiation or transdifferentiation. Another object of the present invention is the use of a compound or seaweed extract as described herein (e.g., of any formulae herein) for use in the treatment of a cell proliferation disorder or disease, or affect cell differentiation, dedifferentiation or transdifferentiation.

Another object of the present invention is the use of a compound or seaweed extract as described herein (e.g., of any formulae herein) for use in the treatment of a ROS-mediated disorder or disease, or a disease alleviated or prevented through the Nrf2-ARE pathway. Another object of the present invention is where the disease or disorder includes proliferative diseases and disorders, inflammation, cancer, Alzheimer's disease and other neurodegenerative disorders, stroke, chronic kidney disease, type II diabetes, and aging itself, and other diseases mediated through ROS or alleviated or prevented through the Nrf2-ARE pathway.

Pharmaceutical Compositions

In one aspect, the invention provides a pharmaceutical composition comprising the compound or seaweed extract and a pharmaceutically acceptable carrier.

In one embodiment, the invention provides a pharmaceutical composition wherein the compound or seaweed extract is 7(E)-9-keto-octadec-7-enoic acid (1), 7(E)-9-keto-hexadec-7-enoic acid (2), and/or 7(E)-9-keto-octadec-7-enamide (3), and a pharmaceutically acceptable carrier.

In another embodiment, the invention provides a pharmaceutical composition wherein the compound or seaweed extract is an extract from the green alga *Ulva lactuca*, and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound or seaweed extract, in unit dosage form, together with instructions for administering the compound to a subject suffering from or susceptible to a ROS mediated disease or disorder, including proliferative diseases and disorders, inflammation, cancer, stroke, chronic kidney disease, type II diabetes, and aging itself, and other diseases mediated through ROS or alleviated or prevented through the Nrf2-ARE pathway, Alzheimer's disease and other neurodegenerative disorders, memory loss, inducing neurogenesis, enhancing memory retention, enhancing memory formation, increasing synaptic potential or transmission, or increasing long term potentiation (LTP), etc.

In one aspect, the invention provides a kit comprising an effective amount of a compound or seaweed extract, in unit dosage form, together with instructions for administering the compound to a subject suffering from or susceptible to a cell proliferation disease or disorder, including cancer, solid tumor, angiogenesis, etc.

In one aspect, the invention provides a kit comprising an effective amount of a compound or seaweed extract, in unit dosage form, together with instructions for administering the compound to a subject suffering from or susceptible to a disease or disorder alleviated or prevented through the Nrf2-ARE pathway, including proliferative diseases and disorders, inflammation, cancer, stroke, chronic kidney disease, type II diabetes, and aging itself, and other diseases mediated through ROS or alleviated or prevented through the Nrf2-ARE pathway, Alzheimer's disease and other neurodegenerative disorders, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

Topical administration of the pharmaceutical compositions of this invention is especially useful when the desired treatment involves areas or organs readily accessible by topical application. For topical application topically to the skin, the pharmaceutical composition should be formulated with a suitable ointment, lotion, or cream containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

For topical administration, the active compound(s), extracts, enriched extracts, or prodrug(s) can be formulated as solutions, gels, ointments, creams, suspensions, and the like.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

HPLC was carried out on a Shimadzu Prominence Series. $^1$H and 2D NMR data in CDCl$_3$ were recorded on a Bruker Avance II 600 MHz NMR spectrometer using a 5-mm TXI cryogenic probe. The $^{13}$C NMR data was recorded at 125 MHz on a Bruker 500 MHz NMR spectrometer. All spectra were referenced to residual solvent signals ($\delta_H$ 7.26 ppm and/or $\delta_C$ 77.16 ppm). UV absorbance was measured in a sub-micro (50 µl) quartz cuvette (Starna cells) using a SpectraMax M5 (Molecular Devices) spectrophotometer. Accurate mass (HRESIMS) data was obtained on an Agilent 6210 TOF LC-TOF mass spectrometer equipped with an APCI/ESI multimode ion source detector.

Example 1: Extraction and Isolation of Compounds 1, 2, and 3

*Ulva lactuca* was collected from Shark Island (N 27° 28.024, W 80° 19.163) near Fort Pierce, Fla., on Jul. 25, 2006 and Jun. 3, 2009. They were immediately frozen on dry ice, then stored at −20° C. until lyophilized. The dried samples in a glass flask equipped with a magnetic stirring bar (Fisherbrand® Egg-shape, 14-513-55, 0.75 in ×2.5 in) were extracted with agitation (Corning® Digital Stirring Hot Plate [Model PC-420D], 700 rpm) in 200×(w/v) of a nonpolar solvent combination (50% EtOAc in MeOH, v/v) at room temperature for 24 h. At the end of the extraction, the solvents were removed by a Rotavapor® (BÜCHI Labortechnik AG), and the resulting extracts stored at 4° C. until used. The dried extract (2.3 g) was then purified via flash silica gel (2300 g, 170-400 mesh) chromatography (column dimensions: 35 mm×500 mm) where 7 fractions were collected (each fraction was 2 column volumes) using the following solvent systems: 100% DCM, 2% iPrOH/DCM, 5% iPrOH/DCM, 8% iPrOH/DCM, 10% iPrOH/DCM, 20% iPrOH/DCM, and 100% MeOH. Each fraction was concentrated to dryness and stored −20° C. until used to yield: Fr 1 (6.9 mg), Fr 2 (6.9 mg), Fr 3(10.9 mg), Fr 4 (81 mg), Fr 5 (21.1 mg), Fr 6 (14 mg), and Fr 7 (1726.5 mg). Fr 4 (the 8% iPrOH/DCM fraction) and Fr 5 (10% iPrOH/DCM fraction) were purified via semi-preparative HPLC (Column: Phenomenex Synergi Hydro-RP, 250 mm×10 mm, 4 µM; Flow rate=2.0 ml/min) eluting with ACN/water (10%-100% ACN/water from 0-40 min; then 100% ACN from 40-60 min) to afford, after concentration, two products with $t_R$=41.2 min and $t_R$=42.8 min, respectively. The two fractions were each separately purified via analytical reverse-phase HPLC (Column: Restek Allure C18, 250 mm×4.6 mm, 5 mM; Flow rate=1.0 ml/min) eluting with ACN/water (10%-100% ACN/water with 0.1% formic acid from 0-20 min; then 100% ACN from 20-25 min with 0.1% formic acid). The purification of the $t_R$=41.2 min fraction afforded two separated products, Compounds 1 (0.5 mg, $t_R$=21.9 min) and 2 (0.2 mg, $t_R$=19.7 min), each as colorless amorphous solids. The purification of the $t_R$=42.8 min fraction afforded Compound 3 (0.1 mg, $t_R$=20.4 min) as a colorless amorphous solid. The reported amounts of each of the three compounds were the result of resubjecting the remaining silica gel fractions (i.e. Fr 3 and Fr 6) to the above process: 1) concentration of Fr 3 and Fr 6, 2) purifying the combined residues via semi-preparative HPLC, followed by analytical HPLC purification.

7(E)-9-keto-octadec-7-enoic acid (1): 0.5 mg, colorless, amorphous solid; UV (EtOH) $\lambda_{max}$ (log $\epsilon$) 210 (2.46); HRESIMS m/z 319.2247 for [M+Na]$^+$ (calculated for $C_{18}H_{32}O_3$, 319.2244); $^1$H NMR, $^{13}$C NMR, and 2D NMR data, see Table 1.

7(E)-9-keto-hexadec-7-enoic acid (2): 0.2 mg, colorless, amorphous solid; UV (EtOH) $\lambda_{max}$ (log $\epsilon$) 212 (2.41); $^1$H NMR, $^{13}$C NMR, and 2D NMR data, see Table S2; HRESIMS m/z 291.1942 for [M+Na]$^+$ (calculated for $C_{16}H_{28}O_3$, 291.1931).

7(E)-9-keto-octadec-7-enamide (3): 0.1 mg, colorless, amorphous solid; UV (EtOH) $\lambda_{max}$ (log $\epsilon$) 209 (2.46); $^1$H NMR, $^{13}$C NMR, and 2D NMR data, see Table 1; HRESIMS m/z 318.2417 for [M+Na]$^+$ (calculated for $C_{18}H_{33}NO_2$, 318.2404).

Figure 1B:
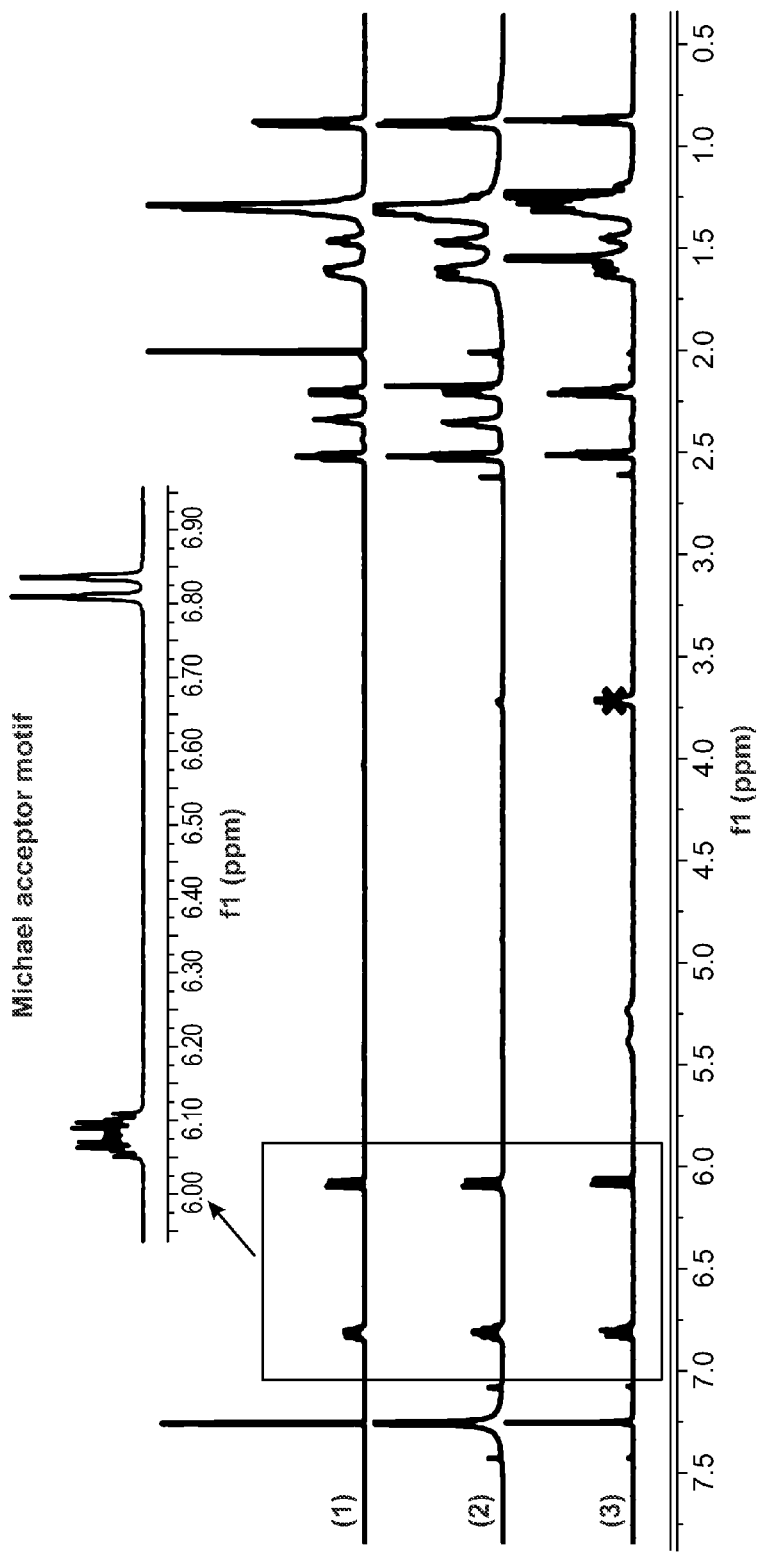
FIG. 1B. depicts the $^1$H NMR signals for compounds 1-3 in $CDCl_3$ at 600 MHz. Structural information of the three compounds isolated from *Ulva lactuca*. (B) 1H NMR characteristic signals for compound 1-3 in CDCl3 recorded at 600 MHz.

[M+Na]$^+$ of 319.2247, suggesting a molecular formula of $C_{18}H_{32}O_3$, with three degrees of unsaturation. The chemical structure was elucidated by 1D ($^1$H and $^{13}$C) and 2D (COSY, TOCSY, HSQC, and HMBC) NMR techniques (Table 1). The $^1$H NMR spectrum was indicative of a fatty acid type molecule, with signals for a methylene envelope ($\delta_H$ 1.30, 12H, C12-C17) and a poorly defined triplet due to a terminal —CH$_3$ ($\delta_H$ 0.88, H$_3$-18) with virtual coupling (FIG. 1B). The two olefinic protons between $\delta_H$ 6-7 ppm ($\delta_H$ 6.83, H-7 and $\delta_H$ 6.08, H-8) appeared to have HMBC correlations to a ketone carbonyl carbon at $\delta_C$ 201.24 (C9), constituting an α,β-unsaturated carbonyl system. The trans conformation of the double bond was deduced based on the large coupling constant (15.8 Hz) between the olefinic protons (H-7 and H-8). The third degree of unsaturation was accounted for by a carboxylic acid carbonyl group at $\delta_C$ 177.20 (C1).

Compound 2, 7(E)-9-keto-hexadec-7-enoic acid, possessed a $^1$H NMR spectrum very similar to that of 1, indicating that it is also a fatty type molecule (FIG. 1B).

TABLE 1

NMR data for 7(E)-9-keto-octadec-7-enoic acid (1) and 7(E)-9-keto-octadec-7-enamide (3) in CDCl$_3$.

| | 7(E)-9-keto-octadec-7-enoic acid (1) | | | 7(E)-9-keto-octadec-7-enamide (3) | | |
|---|---|---|---|---|---|---|
| C/H No. | $\delta_C{}^a$ | $\delta_H$ (J, Hz)$^b$ | HMBC$^c$ | $\delta_C{}^d$ | $\delta_H$ (J, Hz)$^b$ | HMBC$^c$ |
| NH | — | — | — | — | 5.39 br s | |
| NH | — | — | — | — | 5.24 br s | |
| 1 | 177.20 qC | — | — | 175.36 qC | — | |
| 2 | 33.78 CH$_2$ | 2.34 t (7.1) | 3, 1 | 35.22 CH$_2$ | 2.21 t (6.5) | 3, 1 |
| 3 | 24.72 CH$_2$ | 1.63 m | 1, 2 | 24.68 CH$_2$ | 1.63 m | 1, 2 |
| 4 | 31.71 CH$_2$ | 1.31 m | 3 | 28.44 CH$_2$ | 1.33 m | 3 |
| 5 | 27.92 CH$_2$ | 1.46 m | 4, 6 | 27.48 CH$_2$ | 1.46 m | 4, 6 |
| 6 | 32.49 CH$_2$ | 2.21 dt (6.9, 7.0) | 5, 7, 8 | 31.92 CH$_2$ | 2.19 dt (6.9, 7.3) | 5, 7, 8 |
| 7 | 146.46 CH | 6.83 dt (15.8, 6.9) | 5, 6, 9 | 147.58 CH | 6.81 dt (15.9, 6.9) | 5, 6, 9 |
| 8 | 130.87 CH | 6.08 d (15.8) | 6, 9 | 130.26 CH | 6.07 d (15.9) | 6, 9 |
| 9 | 201.24 qC | — | | 200.80 qC | — | |
| 10 | 40.24 CH$_2$ | 2.52 td (7.4, 1.4) | 11, 9, 12 | 39.43 CH$_2$ | 2.50 td (7.4, 1.6) | 11, 9, 12 |
| 11 | 24.34 CH$_2$ | 1.60 m | 10, 9, 12 | 23.56 CH$_2$ | 1.60 m | 10, 9, 12 |
| 12-17 | 29.19 CH$_2$ | 1.30 m | | 28.71 CH$_2$ | 1.31 m | |
| 18 | 14.11 CH$_3$ | 0.88 m | 17 | 13.50 CH$_3$ | 0.88 m | 17 |

$^a$$^{13}$C NMR data was recorded at 125 MHz.
$^b$$^1$H NMR data was recorded at 600 MHz.
$^c$Long range heteronuclear correlations between the indicated carbon and the protons at 600 MHz.
$^d$$^{13}$C data was deduced from HMBC and HSQC.

TABLE S2

NMR data for 7(E)-9-keto-hexadec-7-enoic acid (2) in CDCl$_3$ at 600 MHz.

| C/H No | $\delta_C{}^a$ | $\delta_H$ (J) | HMBC$^b$ |
|---|---|---|---|
| 1 | 176.17 qC | — | — |
| 2 | 32.92 CH$_2$ | 2.35 t (7.2) | 3, 1 |
| 3 | 24.25 CH$_2$ | 1.64 m | 1, 2 |
| 4 | 29.28 CH$_2$ | 1.30 m | 3 |
| 5 | 27.48 CH$_2$ | 1.47 m | 4, 6 |
| 6 | 32.06 CH$_2$ | 2.21 dt (7.0, 7.1) | 5, 7, 8 |
| 7 | 146.90 CH | 6.82 dt (15.9, 7.0) | 5, 6, 9 |
| 8 | 129.96 CH$_2$ | 6.09 d (15.9) | 6, 9 |
| 9 | 201.45 qC | — | |
| 10 | 39.27 CH$_2$ | 2.52 t (7.4) | 11, 9, 12 |
| 11 | 23.90 CH$_2$ | 1.60 m | 10, 9, 12 |
| 12-15 | 28.52 CH$_2$ | 1.32 m | |
| 16 | 13.62 CH$_3$ | 0.89 m | 15 |

$^a$$^{13}$C data was deduced from HMBC and HSQC.
$^b$Long range heteronuclear correlations between the indicated carbon and the protons.

The following captures the analytical efforts involved in the structure elucidation of Compounds 1, 2, and 3.

For compound 1, 7(E)-9-keto-octadec-7-enoic acid, the HRESIMS spectrum showed a pseudomolecular ion HRESIMS analysis showed a pseudomolecular ion [M+Na]$^+$ of 291.1942, with a 28-amu (2×CH$_2$) difference from compound 1. The molecular formula was calculated as $C_{16}H_{28}O_3$. The structure was determined by NMR (Table S2). It was shown that compound 2 has the same exact functionalities as compound 1, including a terminal carboxylic acid group (C1) and an α,β-unsaturated carbonyl system (C7-C 9), but with a truncated fatty chain (C10-C16). This acid had previously been isolated from a laboratory-cultured marine diatom, *Skeletonema marinoi* [31].

Compound 3, 7(E)-9-keto-octadec-7-enamide, showed a pseudomolecular ion [M+Na]$^+$ of 318.2417 by HRESIMS, with only 1-amu difference from acid 1. Its molecular formula was calculated as $C_{18}H_{33}NO_2$, also with three degrees of unsaturation. The structure was determined again by NMR (Table 1). While the same α,β-unsaturated carbonyl system (C7-C9) and the fatty chain (C10-C18) were observed in the $^1$H NMR spectrum, there was an additional pair of broad, low-field proton signals at $\delta_H$ 5.39 and $\delta_H$ 5.24. These two protons were suggestive of a primary amide moiety at the C1 position in place of the carboxylic acid group present in the other two compounds (FIG. 1B).

Example 2: Extraction and Isolation of *Ulva lactuca* Seaweed Compound 1-Enriched Extract

*Ulva lactuca* was collected from Shark Island (N 27° 28.024, W 80° 19.163) near Fort Pierce, Fla., on Jun. 3, 2009. They were immediately frozen on dry ice, then stored at −20° C. until lyophilized. The dried samples in a glass flask equipped with a magnetic stirring bar (Fisherbrand® Egg-shape, 14-513-55, 0.75 in ×2.5 in) were extracted with agitation (Corning® Digital Stirring Hot Plate [Model PC-420D], 700 rpm) in 200×(w/v) of a non-polar solvent combination (50% EtOAc in MeOH, v/v) at room temperature for 24 h. At the end of the extraction, the solvents were removed by a Rotavapor® (BÜCHI Labortechnik AG), and the resulting extract stored at 4° C. until used. The concentrated extract was partitioned between EtOAc and water, the phases were separated, and the EtOAc layer was concentrated in vacuo. The residue was then purified via flash silica gel chromatography, where 6 fractions were collected using the following solvent systems: 20% EtOAc, 50% EtOAc/Hex, 75% EtOAc/Hex, 100% EtOAc, 80% EtOAc/MeOH, and 100% MeOH. Each fraction was analyzed via analytical reverse-phase HPLC (described above). The 75% EtOAc/Hex fraction (Fr 3*) was the only fraction that contained compound 1. The identity of compound 1 in this fraction was confirmed by HPLC co-injection, NMR and mass spectrometry.

Example 3: Cell Culture

IMR-32 (human neuroblastoma) cells (ATCC) were cultured in Eagle's Minimum Essential Medium (EMEM, ATCC) supplemented with 10% (v/v) fetal bovine serum (FBS, HyClone) and 1% (v/v) antibiotic-antimycotic (Invitrogen). The cells were maintained at 37° C. in a humidified 5% carbon dioxide ($CO_2$) atmosphere.

Example 4: ARE-Luc Reporter Assay and Results

IMR-32 cells (33,000 cells/well) were transiently transfected with ARE-luc plasmid (100 ng/well) using FuGENE® HD (Roche Diagnostics) as a transfection reagent (1:3, w/v). The cells were dispensed into each well of a 96-well plate and incubated for 24 h. They were then treated with solvent control (DMSO or EtOH, 1%, v/v) or individual extracts/fractions/compounds for 24 h before ARE activities were detected by using BriteLite detection reagent (PerkinElmer). Relative fold activation for the treated samples over solvent control was reported. The ARE-luciferase (ARE-luc) reporter contains the ARE sequence of human NQO1: 5'-CTCAGCCTTC-CAAATCGCAGTCACAGTGACTCAGCAGAATC-3' [Moehlenkamp, J. D.; Johnson, J. A. Activation of antioxidant/electrophile-responsive elements in IMR-32 human neuroblastoma cells. *Arch Biochem Biophys.* 363:98-106; 1999].

Example 5: Immunoblot Analysis and Results

IMR-32 cells (800,000 cells/well) were seeded into each well of 6-well plates. 24 h later, cells were treated with solvent control (EtOH, 0.5%, v/v) or fractions/compounds. After another 24 h, whole cell lysates were collected in PhosphoSafe buffer (Novagen) following the manufacturer's protocol and stored at −80° C. until analyzed. For each sample, the protein concentration was measured using a BCA assay kit (Pierce). Samples containing equal amount of total protein were separated by SDS-PAGE (NuPAGE® Novex® 4-12% Bis-Tris Mini gels, Invitrogen), transferred onto a PVDF membrane, and incubated overnight with the indicated primary antibodies at 4° C. on an orbital shaker. The membranes were then incubated with the corresponding secondary antibodies (HRP-linked) for 1 h at room temperature and detected with Supersignal Femto Western Blotting kit (Pierce). Anti-NQO1 (mouse) antibody was from Abcam; anti-β-actin (rabbit), anti-mouse-HRP, and anti-rabbit-HRP antibodies were from Cell Signaling Technology.

For assays in the presence of an antioxidant, the cells were pretreated with excess NAC (1 mM, pH 7.50) for 2 h before they were treated with solvent control or the compounds (see above). For kinase inhibitor assays, the cells were pretreated with the previously established active concentrations of the corresponding inhibitors, LY294000 (25 µM) or PD98059 (50 µM) [Wang, R.; Kern, J. T.; Goodfriend, T. L.; Ball, D. L.; Luesch, H. Activation of the antioxidant response element by specific oxidized metabolites of linoleic acid. *Prostaglandins Leukot Essent Fatty Acids.* 81:53-9; 2009.1, for 30 min before being treated with the solvent control or compounds (see above).

Example 6: RNA Extraction, cDNA Synthesis, and Quantitative PCR (qPCR) Analysis Cultured cells were treated in the same way as described for the immunoblot experiments. After 12 h, total RNA was extracted using a commercial kit (RNeasy Mini Kit, Qiagen). For mice tissues, total RNA was extracted using TRIzol® reagent (Invitrogen) following the standard manufacturer's protocol.

cDNA synthesis and qPCR experiments for both cultured cells and mice tissues were performed following the same procedure. 2 µg of each RNA sample was reverse-transcribed into cDNA, which served as a template for Tag-Man® gene expression assays (Applied Biosystems). For each qPCR run, a total reaction volume of 25 µl was prepared consisting of 12.5 µl of TaqMan 2× universal master mix, 1.25 µl of a 20× TaqMan gene expression assay probe, 1 µl of cDNA and 10.25 µl of RNase-free sterile water. The reactions were dispensed into 96-well optical reaction plates (Applied Biosystems) and detected in an Applied Biosystems® 7300 Real-Time PCR System. The thermocycler program consisted of 2 min at 50° C., 10 min at 95° C., and 40 cycles of 95° C. for 15 s and 60° C. for 1 min. For normalization, GAPDH expression was used as an internal control for human cells (IMR-32) and β-actin for mice tissue samples.

Example 7: RNA Interference Experiments

IMR-32 cells (600,000 cells/well) were seeded in 6-well plates and incubated at 37° C. for 24 h. The medium was then carefully aspirated and replaced with a transfection mixture containing siRNAs (50 nM) and siLentFect™ lipid transfection reagent (Bio-Rad Laboratories) in fresh medium (2 ml/well). 48 h after transfection, the cells were treated with solvent control (EtOH, 0.5%, v/v) or compound 1 for 24 h. The treated cells were then lysed in PhosphoSafe buffer and whole cell lysates analyzed by immunoblot (see above). The siRNAs, siGENOME Non-Targeting siRNA Pools and siGENOME SMARTpool (human NFE2L2), were purchased from Dharmacon.

Example 8: Glutathione Assays

Glutathione assays were performed following the manufacturer's protocol (Sigma). Briefly, IMR-32 cells (800,000 cells/well) were seeded into 6-well plates and incubated at 37° C. The cells were then treated with solvent control (EtOH, 0.5%, v/v) or compound 1 for the indicated period of time. At the end of each treatment, the cells were washed twice with Dulbecco's phosphate buffered saline (DPBS), harvested in 200 µl of DPBS, and pelleted at 600×g for 10 min at 4° C. After removal of DPBS, the cell pellet was deproteinized and re-suspended in 3 volumes of 5% sulfosalicylic acid solution (v/v). The suspension was frozen (liquid $N_2$) and thawed (37° C. water bath) twice and then incubated at 4° C. for 5 min. The cell debris was spun down at 10,000×g for 10 min at 4° C. The supernatant was transferred to fresh tubes and used as glutathione stock. The concentration of the total glutathione (GSH+GSSG) was measured and compared with a standard curve of reduced glutathione (GSH).

Example 9: Mice Studies

All animal experiments conducted were approved by the Institutional Animal Care & Use Committee at the University of Florida. The transgenic mice (B6C3-ARE-Tg) were obtained from Professor J. Johnson [Johnson, D. A.; Andrews, G. K.; Xu, W.; Johnson, J. A. Activation of the antioxidant response element in primary cortical neuronal cultures derived from transgenic reporter mice. *J Neurochem.* 81:1233-41; 20021, bred by the Animal care services at UF and genotyped at Professor D. Borchelt's lab. The mice were housed in a pathogen-free environment and inspected daily. Three male mice (3-4 months old) were used in each treatment group. Fraction 3* was prepared in a vehicle consisting of 10% DMSO (v/v), 10% Cremophor-EL (v/v) in PBS as a 10 mg/ml suspension. A single dose of 200 µl (50 mg/kg) was administered by oral gavaging. No apparent toxicity was observed for any animal. After 12 h, the mice were euthanized in 100% $CO_2$. The tissues were harvested immediately, frozen on dry ice, and kept at −80° C. until analyzed.

Example 10: hPAP Assay

The frozen tissues were thawed on ice and lysed in TMNC buffer (0.05 M Tris-HCl, 0.005 M $MgCl_2$, 0.1 M NaCl, 1% CHAPS (w/v), pH 7.0 [Kraft, A. D.; Johnson, D. A.; Johnson, J. A. Nuclear factor E2-related factor 2-dependent antioxidant response element activation by tert-butylhydroquinone and sulforaphane occurring preferentially in astrocytes conditions neurons against oxidative insult. *J Neurosci.* 24:1101-12; 20041. The homogenized samples were centrifuged at 16,100×g for 2 min at 4° C. The supernatants were transferred to fresh tubes and used as hPAP stock. hPAP activity in each sample was determined by using a commercial kit (Phospha-Light™ system). Briefly, the protein concentration in each sample was measured using the BCA assay. 100 µl of protein (300 µg) was diluted with equal volume of 1× assay buffer and incubated at 65° C. for 30 min to inactivate any endogenous alkaline phosphatase activity. The heated samples were then cooled on ice to room temperature and dispensed into 96 well plates (50 µl/well). 50 µl of assay buffer (room temperate) was added to each well and incubated for 5 min before addition of reaction buffer (50 µl/well, room temperature). The reaction was incubated for another 20 min and detected for luminescence (0.25 sec/well). The average hPAP activities of a set of mice (n=3) that did not carry the transgene was used as an internal control for normalization and subtracted from each value obtained for transgenic mice.

Biological Results

Figure 2:
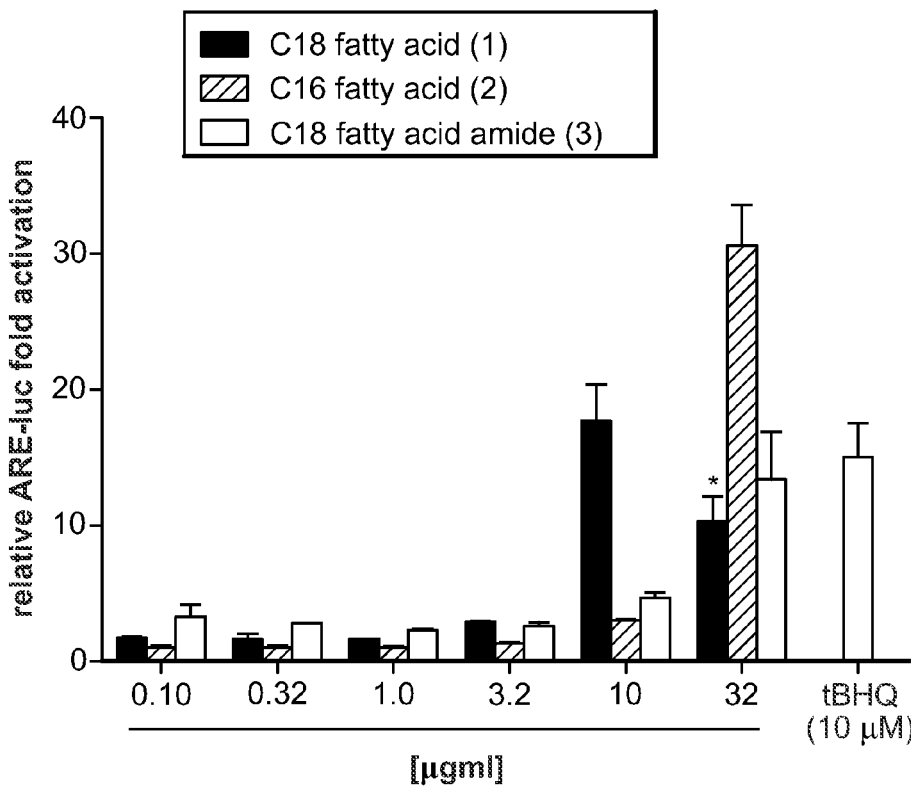
FIG. 2. depicts the dose-dependent ARE-luc activities of compounds 1-3 in IMR-32 cells. Structure/activity relationship analysis for compound 1. Dose-dependent ARE-luc activities of the three compounds in IMR-32 cells (n=3).

The ARE activities of the three compounds in IMR-32 cells were compared by dose-response analysis using the reporter gene assay (FIG. 2). At 10 µg/ml, the C18 fatty acid (1) showed remarkable ARE activation (17.6-fold), which was six times higher than the C16 acid (2, 2.8-fold), four times higher than the fatty acid amide (3, 4.5-fold), and even slightly higher than the positive control (tBHQ, 14.9-fold). At the higher concentration tested, 32 µg/ml, the C18 acid (1) showed signs of cytotoxicity, while the other two strongly activated the reporter. At 32 µg/ml, the C16 acid (2) was two times more efficacious than the fatty acid amide (3) (30.3-fold vs. 13.2-fold, respectively).

Figure 3:
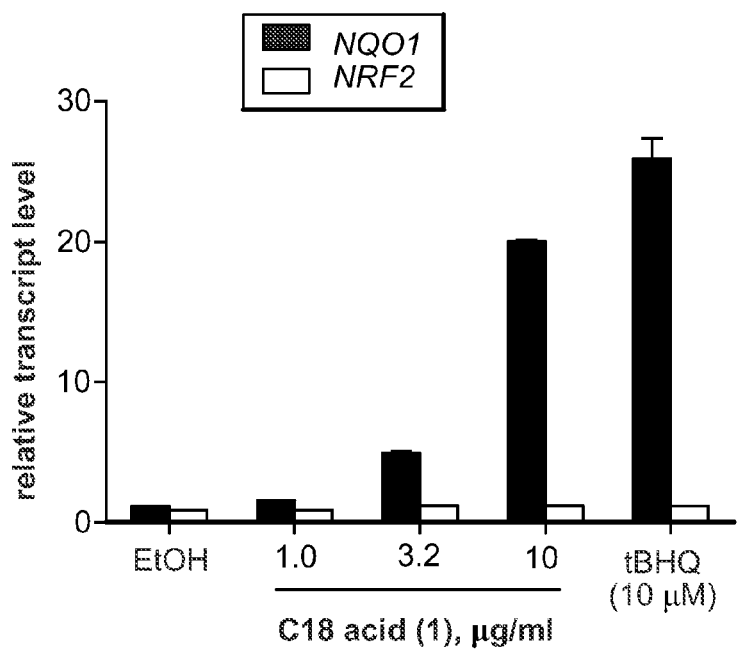
FIG. 3. depicts the dose-dependent increase of NQO1 mRNA levels without an increase in NRF2 mRNA levels after 12 h of treatment with compound 1. Compound 1 induces cytoprotective genes in IMR-32 cells. (A) Treatment with compound 1 led to dose-dependent increase in NQO1, but not NRF2, mRNA levels after 12 h (n=3).
Figure 4:
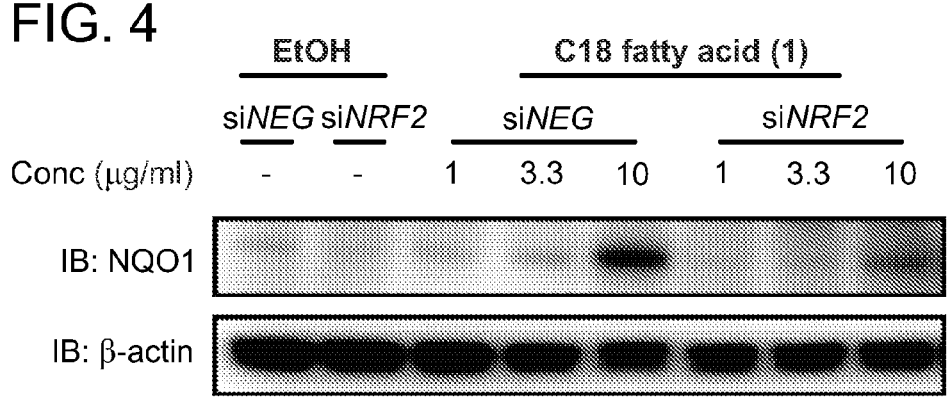
FIG. 4. depicts the dependency of compound 1-induced NQO1 expression on NRF2. Compound 1 requires NRF2 and PI3K for the induction of ARE-regulated genes in IMR-32 cells. (A) NRF2 is essential for compound 1-induced NQO1 expression. The cells were incubated for 48 h after siRNA transfection, then treated with compound 1 for 24 h before whole cell lysates were collected.

The levels of an endogenous ARE-regulated cytoprotective gene, NQO1, in IMR-32 cells upon exposure to the C18 fatty acid (1) were assessed. The induction of NQO1 was found to be dose-dependent both at the transcript and protein levels. Higher than basal levels of NQO1 mRNA were detected starting from 1 µg/ml (1.5-fold), and were much more pronounced at the higher non-toxic concentrations (FIG. 3). Similarly, by immunoblot analysis, NQO1 protein expression was detectable starting at 1 µg/ml and was the highest at 10 µg/ml (FIG. 4).

Figure 5:
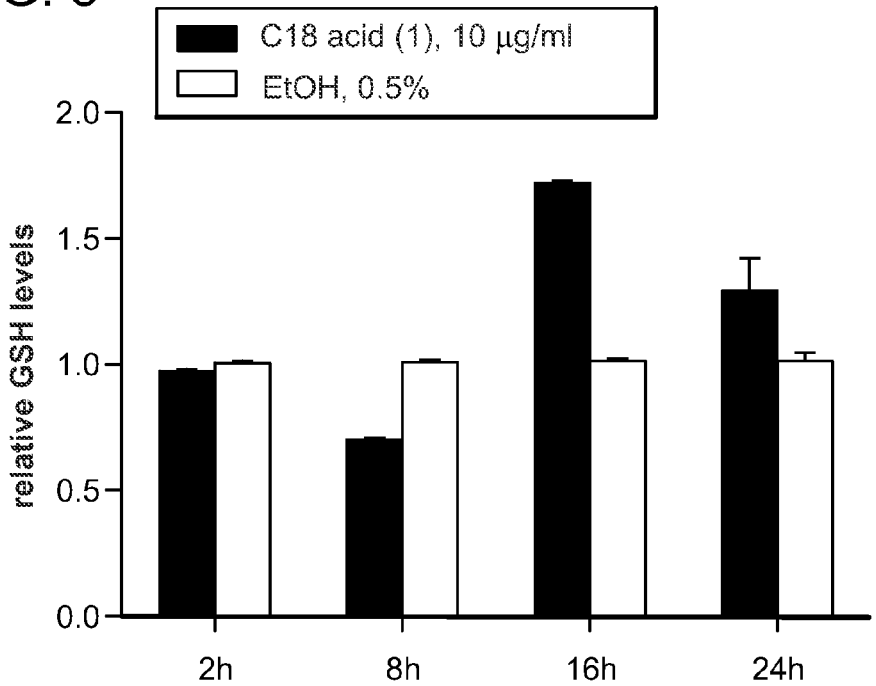
FIG. 5. depicts the net increase of glutathione levels after treatment with compound 1 in IMR-32 cells. Compound 1 induces cytoprotective genes in IMR-32 cells. (C) Compound 1 induced a net increase in glutathione levels at its active concentration (n=3). Following a decrease (~30%) until 8 h, GSH levels started to increase and peaked at 16 h, then dropped back but stayed above the basal level up to at least 24 h. The results for the ARE-luc assay are shown as fold activation±SEM; the qPCR and GSH results are fold activation±standard deviation (SD).

Next, the levels of endogenous glutathione over time were examined after the cells were treated with compound 1. While a transient decrease was observed until 8 h (<30%), confirming reactivity towards GSH, the level of glutathione was restored by more than 50% of the basal level at 16 h and stayed above baseline at least up to 24 h (FIG. 5), which is consistent with increased GSH biosynthesis via induced biosynthetic gene transcription.

ARE activation is tightly regulated by Nrf2 and Keap1. In a healthy cell, Nrf2, the transcriptional activator of the ARE, is targeted by its cytoplasmic repressor, Keap1, for proteasomal degradation. When Keap1 senses environmental stress or harmful chemicals, it releases Nrf2, which translocates to the nucleus, where it binds to the ARE and activates expression of downstream cytoprotective genes.

As shown in FIG. 3, the levels of NRF2 mRNA remained unchanged at the effective doses (1-10 µg/ml) of compound 1, indicating that the induction of ARE-regulated genes was not due to an elevated NRF2 transcript level. To confirm the involvement of NRF2 in fatty acid 1-induced ARE activation, we used small interfering RNAs (siRNAs) to knock down endogenous NRF2 transcripts in IMR-32 cells [Wang, R.; Kern, J. T.; Goodfriend, T. L.; Ball, D. L.; Luesch, H. Activation of the antioxidant response element by specific oxidized metabolites of linoleic acid. *Prostaglandins Leukot Essent Fatty Acids.* 81:53-9; 2009.1. The NRF2-depleted cells were then treated with 1 and analyzed for the expression of the ARE-regulated NQO1 (FIG. 4). NQO1 was virtually undetectable by immunoblot analysis, suggesting that NRF2 is essential for fatty acid 1-induced cytoprotective gene expression.

Figure 6:
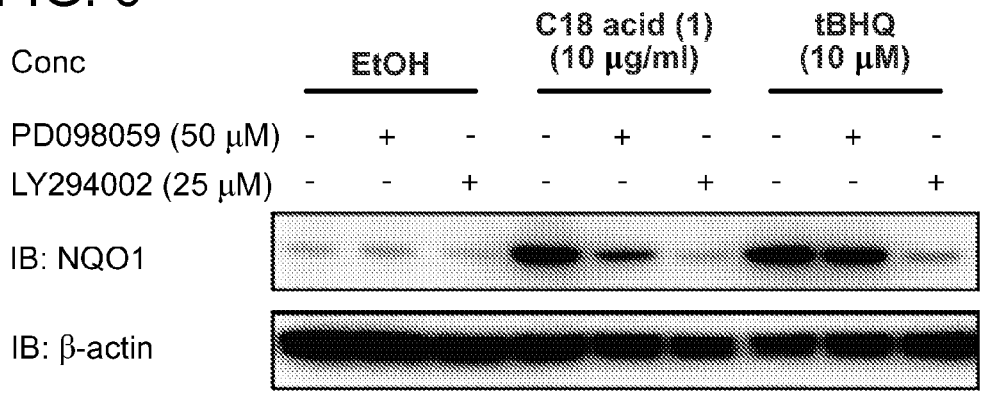
FIG. 6. depicts the dependency of compound 1-induced NQO1 expression on PI3K activity. PI3K activity is required for induction of NQO1 expression by compound 1. 50 μM of PD098059 (a MEK1 inhibitor) or 25 μM of LY294002 (a PI3K inhibitor) was used to pre-treat the cells for 30 min before they were exposed to 10 μg/ml of compound 1. After another 24 h of incubation, whole cell lysates were prepared and assessed for NQO1 expression by immunoblot analysis.

Loss-of-function experiments were performed to investigate the kinase requirements for fatty acid 1-induced ARE activation. IMR-32 cells were pre-treated with pharmacological inhibitors of either the PI3K or the MAPK pathway for 30 min, before being exposed to fatty acid 1 at its active concentration (10 µg/ml). After 24 h, the cells were lysed and analyzed by Western blot. Expression of NQO1 was induced by the compound in the presence of a MAPK (MEK1) inhibitor, but not a PI3K inhibitor (FIG. 6). These data indicated that PI3K is required for the induction of ARE-regulated genes by compound 1 in IMR-32 cells.

Figure 7A:
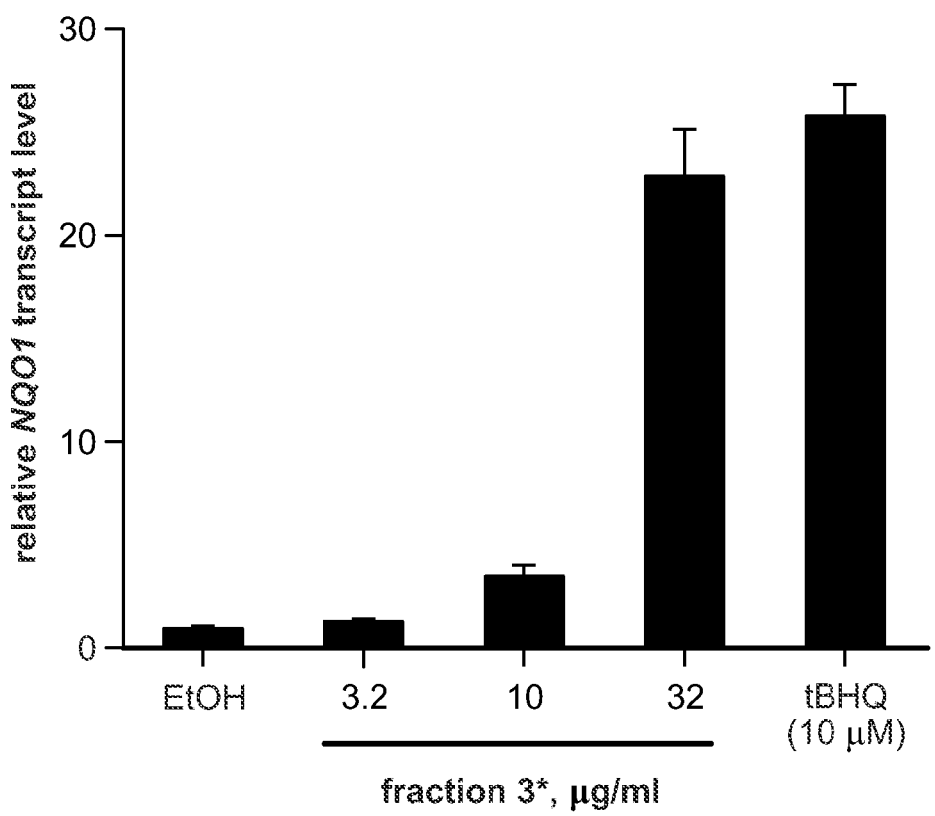
FIG. 7A. depicts the increase in endogenous NQO1 mRNA levels in human IMR-32 cells after 12 h of treatment with fraction 3*. A compound 1-containing Ulva lactuca fraction (fraction 3*, see Materials and Methods) induces the cytoprotective gene Nqo1 in vitro and in vivo. (A) Fraction 3* increased endogenous NQO1 mRNA levels in human IMR-32 cells after 12 h of treatment (n=3).
Figure 7B:
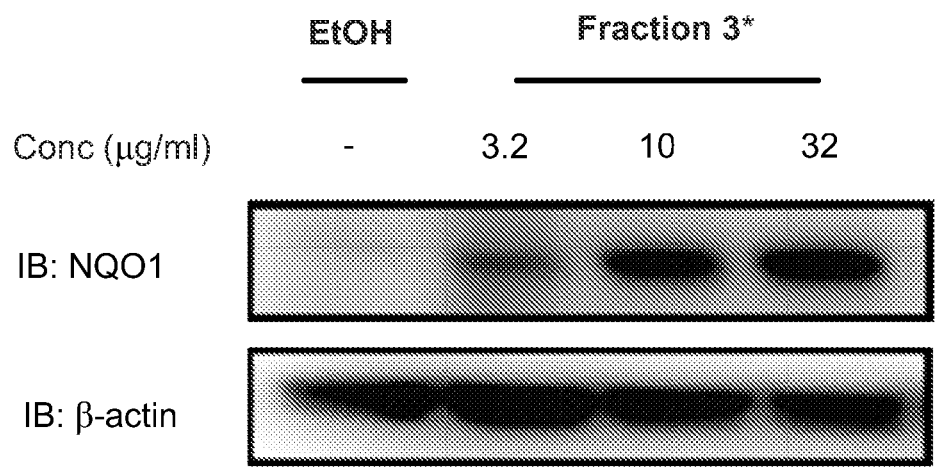
FIG. 7B. depicts the dose-dependent induced expression of NQO1 at the protein level after 24 h of treatment with fraction 3*. A compound 1-containing Ulva lactuca fraction (fraction 3*, see Materials and Methods) induces the cytoprotective gene Nqo1 in vitro and in vivo. (B) Fraction 3* dose-dependently induced expression of NQO1 at the protein level after 24 h of treatment.

The activity of a compound 1-containing *Ulva* fraction in mice was assessed. To ensure that the bioactivity of fraction 3* was comparable to that of compound 1, the endogenous expression of the ARE regulated gene, NQO1, was assessed at the transcript and protein levels in IMR-32 cells. It was shown that fraction 3* induced high levels of NQO1 in a dose-dependent manner. Higher than baseline levels of NQO1 mRNA were detected starting from 3.2 µg/ml (1.4-fold) and continued to increase until 32 µg/ml (23.0-fold) (FIG. 7A); a similar trend was observed at the level of protein expression (FIG. 7B).

Figure 8:
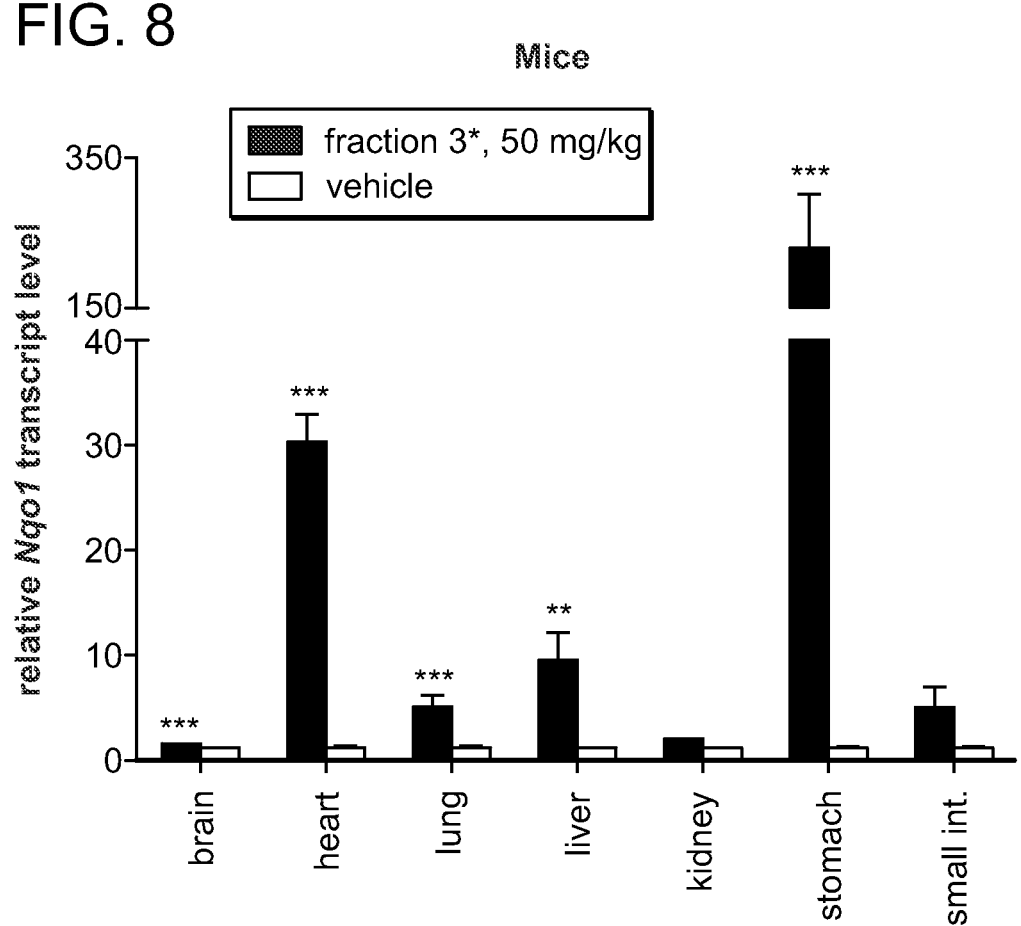
FIG. 8. illustrates that fraction 3* induced Nqo1 expression in multiple tissues in mice. A compound 1-containing Ulva lactuca fraction (fraction 3*, see Materials and Methods) induces the cytoprotective gene Nqo1 in vitro and in vivo. (C) Fraction 3* induced endogenous Nqo1 expression in multiple tissues in mice. A strain of transgenic mice (B6C3-ARE-Tg) was used in this study. The mice (n=3) were fed by oral gavaging and the tissues were collected after 12 h. Each tissue was divided into two identical portions and one set of which was analyzed for Nqo1 mRNA level (for small intestine vehicle mice, n=2). *: $P \leq 0.05$. : $P=0.06$. The results for cellular qPCR assays are fold activation±SD; for mice tissues are shown as fold activation±SEM.

A single dose (50 mg/kg) of the compound 1-containing fraction 3* was administered by oral gavaging to mice carrying a transgene that has the ARE-containing promoter region of rat Nqo1 gene coupled with the human placental alkaline phosphatase (hPAP) reporter [Johnson, D. A.; Andrews, G. K.; Xu, W.; Johnson, J. A. Activation of the antioxidant response element in primary cortical neuronal cultures derived from transgenic reporter mice. *J Neurochem.* 81:1233-41; 2002.; Yates, M. S.; Tauchi, M.; Katsuoka, F.; Flanders, K. C.; Liby, K. T.; Honda, T.; Gribble, G. W.; Johnson, D. A.; Johnson, J. A.; Burton, N. C.; Guilarte, T. R.; Yamamoto, M.; Sporn, M. B.; Kensler, T. W. Pharmacodynamic characterization of chemopreventive triterpenoids as exceptionally potent inducers of Nrf2-regulated genes. *Mol Cancer Ther.* 6:154-62; 20071. After 12 h, the mice were euthanized and various tissues harvested. Each tissue was uniformly divided into two parts and analyzed for the increase in the endogenous Nqo1 mRNA levels and the enzymatic activities of the transgene-encoded hPAP protein. While changes in hPAP activities were not statistically significant (P>0.05), significant induction (P≤0.05) of endogenous Nqo1 was detected in more than half of the seven tissues tested (FIG. 8). Other than expectedly the stomach, the heart tissues showed the highest significant induction (30.3-fold). Significantly elevated levels of Nqo1 were also found in lung (4.8-fold) and the brain (1.3-fold); the activation in the liver was of borderline significance (9.3-fold, P=0.06). Even though not statistically significant (P>0.05) with our sample size, Nqo1 induction in the other tissues (kidney and small intestine) appeared to follow the same trend.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method of treating a human suffering from colon cancer or prostate cancer comprising orally administering a therapeutically effective amount of seaweed *Ulva lactuca* extract to said human suffering from colon cancer or prostate cancer to effectively treat the colon cancer or prostate cancer in the human.

* * * * *